(12) United States Patent
Shi et al.

(10) Patent No.: US 12,310,834 B2
(45) Date of Patent: May 27, 2025

(54) PTMC-BASED INTESTINAL ANASTOMOSIS STENT OF BIOABSORBABLE FLEXIBLE ELASTOMER AND PREPARATION METHOD THEREFOR

(71) Applicant: WENZHOU INSTITUTE, UNIVERSITY OF CHINESE ACADEMY OF SCIENCES, Wenzhou (CN)

(72) Inventors: Changcan Shi, Wenzhou (CN); Xujian Li, Wenzhou (CN); Zhixiao Ji, Wenzhou (CN); Luqi Pan, Wenzhou (CN); Xiao Yang, Wenzhou (CN)

(73) Assignee: Wenzhou Institute, University of Chinese Academy of Sciences, Wenzhou (CN)

( * ) Notice: Subject to any disclaimer, the term of this patent is extended or adjusted under 35 U.S.C. 154(b) by 0 days.

(21) Appl. No.: 18/557,519

(22) PCT Filed: Apr. 25, 2022

(86) PCT No.: PCT/CN2022/088873
§ 371 (c)(1),
(2) Date: Oct. 26, 2023

(87) PCT Pub. No.: WO2022/228356
PCT Pub. Date: Nov. 3, 2022

(65) Prior Publication Data
US 2024/0261124 A1    Aug. 8, 2024

(30) Foreign Application Priority Data
Apr. 30, 2021    (CN) .......................... 202110487743.6

(51) Int. Cl.
| | | |
|---|---|---|
| *A61F 2/04* | (2013.01) | |
| *A61F 2/94* | (2013.01) | |
| *A61L 31/04* | (2006.01) | |
| *A61L 31/06* | (2006.01) | |
| *A61L 31/14* | (2006.01) | |
| *A61L 31/16* | (2006.01) | |

(Continued)

(52) U.S. Cl.
CPC ................. *A61F 2/04* (2013.01); *A61F 2/94* (2013.01); *A61L 31/042* (2013.01); *A61L 31/06* (2013.01);
(Continued)

(58) Field of Classification Search
CPC .... A61L 31/148; A61L 2300/202; A61F 2/04; A61F 2002/044–045; C08G 64/183; D01F 1/103; D01F 6/94
See application file for complete search history.

(56) References Cited

U.S. PATENT DOCUMENTS

| 8,048,168 B2 | 11/2011 | Dillinger |
| 8,445,603 B2 | 5/2013 | Schwartz et al. |

(Continued)

FOREIGN PATENT DOCUMENTS

| CN | 101133973 A | 3/2008 |
| CN | 113288505 A | 8/2021 |

(Continued)

OTHER PUBLICATIONS

Ajiro, Hiroharu, et al., "Polymer design using trimethylene carbonate with ethylene glycol units for biomedical applications," *Polymer Journal*, vol. 48, No. 7, pp. 751-760 (Apr. 2016).

*Primary Examiner* — William H Matthews
(74) *Attorney, Agent, or Firm* — Christensen, Fonder, Dardi & Herbert PLLC; John P. Fonder

(57) ABSTRACT

A PTMC-based intestinal anastomosis stent of a bioabsorbable flexible elastomer and a preparation method therefor. The intestinal anastomosis stent that uses PTMC as a base material is prepared by using an electrospinning method, and an appropriate range suitable for being implanted into the body is screened out according to a degradation rate and a mechanical property. The stent is loaded with TCS having a bactericidal effect, so that the stent has a tissue repair (Continued)

adjustment function, enabling a wound to heal more quickly in a severe multi-bacterial intestinal environment, and for adjusting postoperative tissue healing and functional repair. An in-vivo animal intestinal anastomosis experiment is carried out, thus verifying the practical effects and the feasibility of the method.

7 Claims, 6 Drawing Sheets

(51) Int. Cl.
  *D01D 1/02* (2006.01)
  *D01D 1/06* (2006.01)
  *D01D 5/00* (2006.01)
(52) U.S. Cl.
  CPC .............. *A61L 31/148* (2013.01); *A61L 31/16* (2013.01); *D01D 1/02* (2013.01); *D01D 1/065* (2013.01); *D01D 5/0038* (2013.01); *A61L 2300/404* (2013.01)

(56) References Cited

U.S. PATENT DOCUMENTS

| | | | |
|---|---|---|---|
| 9,205,179 | B2 | 12/2015 | Priewe et al. |
| 2006/0212050 | A1* | 9/2006 | D'Agostino ......... A61B 17/072 606/151 |
| 2008/0114466 | A1 | 5/2008 | Shelton |
| 2015/0051687 | A1* | 2/2015 | Dickerhoff ................ A61F 2/86 623/1.11 |

FOREIGN PATENT DOCUMENTS

| | | |
|---|---|---|
| CN | 113413491 A1 | 9/2021 |
| DE | 199 26 008 A1 | 12/2000 |
| JP | 2007-130179 A | 5/2007 |
| JP | 2009-539548 A | 11/2009 |
| JP | 2012-503092 A | 2/2012 |
| JP | 2014-528954 A | 10/2014 |
| JP | 2015-530157 A | 10/2015 |

* cited by examiner

PTMC-BASED INTESTINAL ANASTOMOSIS STENT OF BIOABSORBABLE FLEXIBLE ELASTOMER AND PREPARATION METHOD THEREFOR

RELATED APPLICATIONS

The present application is a National Phase entry of PCT Application No. PCT/CN2022/088873, filed Apr. 25, 2022, which claims priority to Chinese Patent Application No. 202110487743.6, filed Apr. 30, 2021, the disclosures of which are hereby incorporated by reference herein in their entirety.

TECHNICAL FIELD

The present invention specifically relates to the technical field of polymer materials, in particular to a PTMC-based intestinal anastomosis stent of a bioabsorbable flexible elastomer and a preparation method therefor.

BACKGROUND OF THE INVENTION

Gastrointestinal reconstruction anastomosis is one of the most common surgical procedures in abdominal surgery. In the past century of the development of gastrointestinal surgery, the incidence of anastomotic fistula has not decreased significantly, which has become one of the worldwide challenges to the success rate of gastrointestinal surgery. Intestinal lesions such as gastrointestinal benign and malignant tumors, gastrointestinal perforation, gastrointestinal obstruction, hemorrhage and ischemia, often require resection of part of the diseased intestinal tract before anastomosis. Traditional methods mostly use manual suture anastomosis. In recent decades, tubular staplers are mainly used for end-to-end or end-to-side anastomosis, or linear cutter staplers for side-to-side anastomosis. Regardless of the anastomosis procedure, anastomotic fistula, a deadly complication, cannot be prevented.

At present, it is generally accepted and practiced by colorectal surgeons at home and abroad that temporary bypass surgery, such as temporary ileostomy or colostomy and other additional surgeons, can definitely avoid the complications caused by anastomotic fistula, but there is no literature to support whether it can reduce the occurrence probability of anastomotic fistula. However, the bypass surgery requires planned reoperation for reversion, and re-reversion also means re-gastrointestinal reconstruction and anastomosis. There is also the occurrence probability of anastomotic fistula, anastomotic stenosis and other related complications, but the occurrence probability is lower than that of the first operation. Achieving isolation of intestinal contents, especially fecal contents, in the area of the anastomotic stoma with good blood supply at both ends of the anastomotic stoma and without tension in apposition, and achieving relative isolation and a clean local environment are of an effective strategy to prevent anastomotic fistula and complications such as peritonitis and abdominal abscess. The key technical bottleneck of realizing the strategy is the breakthrough of ideal auxiliary anastomosis materials.

The purpose of intestinal anastomosis is to restore the physical, histological and physiological functions of the intestines at both ends of the anastomotic stoma. At present, the main problems of the conventional stapler include that: (1) metal staplers are not biodegradable, resulting in permanent retention in the body; (2) degradable high molecular material staplers lack mechanical matching with wound tissues; and (3) staplers lack the regulation and control functions of tissue repair, and cannot reasonably regulate and control the recovery of normal intestinal functions. Patent of invention CN 111449707A proposes an anorectal stapler, including a handle seat, a transmission assembly, a percussion assembly and an anastomosis-cutting assembly; the transmission assembly includes a screw rod arranged inside the handle seat and an adjustment mechanism arranged at a tail end of the handle seat and connected to the tail end of the screw rod; a nailing seat is fixedly mounted on a front end of the screw rod; the percussion assembly includes a movable handle provided on the handle seat and a straight push rod sheathed on the screw rod; and the anastomosis-cutting assembly includes a staple pusher, a staple cartridge sleeve, a staple cartridge, and a circular knife. In this invention, the staple pusher, the staple cartridge sleeve and the staple cartridge are made of metal materials, so components cannot be degraded in vivo, and can only be permanently retained in vivo or removed by secondary surgery. Patent CN109480943 A is made of a degradable material, adopts a method of nail body perforation and fixation, and designs a support frame at a rear end of a nail body. However, an anastomotic ring has large stiffness and inelasticity, and cannot well adapt to intestinal peristalsis, with obvious foreign body sensation. Similarly, there is a patent of invention CN103230265A, in which the degradable materials polyglycolide and polylactide are used as raw materials for gastrointestinal anastomosis. The stapler has the function of fragile disassembly, but also lacks the mechanical matching with intestinal tissues. An ideal stapler should have the following characteristics: (1) effective isolation of intestinal contents; (2) the operation of stapler implantation having little damage to the intestinal wall of anastomotic stoma; and (3) being easy to operate. The stapling devices currently on the market do not meet the above-mentioned requirements at the same time.

From a production standpoint, stents must be easily manufactured in a variety of different lengths and diameters to accommodate different individuals and do not require any complicated storage procedures. All must meet the requirements while maintaining the economy and affordability of the stent.

SUMMARY OF THE INVENTION

In order to solve the technical defects existing in the prior art, the present invention provides a PTMC-based intestinal anastomosis stent of a bioabsorbable flexible elastomer and a preparation method therefor. The PTMC-based intestinal anastomosis stent has the functions of matching intestinal elasticity, regulating and controlling tissue repair, and can significantly reduce the occurrence probability of intestinal anastomotic fistula and other complications.

The technical solution adopted in the present invention is as follows: a PTMC-based intestinal anastomosis stent of a bioabsorbable flexible elastomer, wherein the intestinal anastomosis stent is integrally made of a PTMC copolymer material, the PTMC copolymer is a polymer material synthesized by a ring-opening polymerization method of a high-molecular medical material PTMC monomer, and a thickness of the intestinal anastomosis stent is 0.05-0.3 mm.

The PTMC copolymer material of the bioabsorbable flexible elastomer intestinal anastomosis stent is loaded with triclosan (TCS).

A plant cellulose tube sleeve is further provided in the intestinal anastomosis stent, the intestinal anastomosis stent is of a gapless sleeve-inlaid structure, a tube made of a plant cellulose material is provided inside, and a PTMC copolymer material is provided outside.

A preparation method for the intestinal anastomosis stent of the bioabsorbable flexible elastomer includes the following steps:

(1) ring-opening polymerization of PTMC: transferring a TMC monomer into a reaction vessel, dissolving a catalyst Sn(Oct)2 in an anhydrous toluene solution under a N2 atmosphere, adding 100 ppm of the solution to a reaction vessel with a pipette for copolymerization to ensure that the whole process is anhydrous and oxygen-free, dissolving the reaction product after 24 h, purifying a polymer solution after complete dissolution, repeating for multiple times, drying the purified copolymer in a vacuum drying oven for 48 h, and then storing the same in a drying cabinet; and (2) preparation of an anastomosis stent by electrospinning: dissolving the dried sample in a $CHCl_3$/DMF mixed solution, the prepared solution having a concentration of 5-10.0%; adding 0.1-1.0 wt % of an antibacterial agent into the mixed solution; after mixing, placing the same on a shaker at 37° C. for sufficient dissolution of the sample to obtain a uniform co-dissolved spinning stock solution; loading the stock solution into a 2.5 ml syringe, the syringe including a metal needle with an inner diameter of 0.5 mm, the sample having a thickness of 0.2±0.01 mm after spinning; and further drying the obtained fiber in the vacuum drying oven at room temperature to remove residual organic solvents and moisture.

In the step (1) the product is dissolved at a condition that $CHCl_3$ or DMF or THF is used for dissolution, the product being placed on a shaker, a temperature of the shaker being set at 37° C.

The purification in the step (1) is performed at a condition that the purification is performed with n-hexane or ethanol and stirring is continuously performed with a glass rod.

$CHCl_3$/DMF in the mixed $CHCl_3$/DMF solution in the step (2) is 1:1.

The spinning step in the step (2) is specifically that a plant cellulose tube sleeve of a certain size is sheathed on an electrospinning receiver for spinning, and a tube of a corresponding size is able to be obtained by controlling parameters, wherein a needle pushing speed V is 1.0-5.0 ml/h, a rotation speed V of a roller is 100-500 RMP, a temperature T is 25-35° C., and a humidity WET is 20-40%.

The present invention has the following beneficial effects: the present invention provides a PTMC-based intestinal anastomosis stent of a bioabsorbable flexible elastomer and a preparation method therefor, wherein the intestinal anastomosis stent that uses PTMC as a base material is prepared by using an electrospinning method, and an appropriate range suitable for being implanted into the body is screened out according to a degradation rate and a mechanical property. The stent is loaded with TCS having a bactericidal effect, so that the stent has a tissue repair adjustment function, enabling a wound to heal more quickly in a severe multi-bacterial intestinal environment, and for adjusting postoperative tissue healing and functional repair. An in-vivo animal intestinal anastomosis experiment is carried out, thus verifying the practical effects and the feasibility of the method.

DETAILED DESCRIPTION OF THE INVENTION

Figure 1:
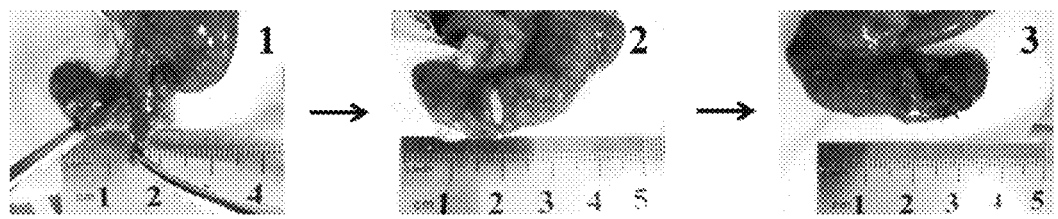
FIG. 1 is an in vivo experimental procedure; (1) Cecal incision; (2) Implantation of anastomosis stent; and (3) Interrupted full-thickness suture.

The technical solutions in the embodiments of the present invention will be described clearly and completely in conjunction with the accompanying drawings in the embodiments of the present invention. Apparently, the described embodiments are merely some embodiments, rather than all embodiments, of the present invention. Based on the embodiments of the present invention, all other embodiments derived by a person of ordinary skill in the art without creative efforts shall fall within the protection scope of the present invention.

Materials

Poly (ethylene glycol) (PEG, Mn=5000), stannous octoate ((Sn(Oct)$_2$), tetrahydrofuran (THF), N,-dimethylformamide (DMF), trichloromethane ($CHCl_3$), triclosan (TCS), toluene, n-hexane, lipase (Lipase from *Aspergillus oryzae*; solution, ≥100,000 U/g) were purchased from Sigma-Aldrich Co. LLC. Polymer grade 1,3-trimethylene carbonate (TMC, Daigang Biology, China). All reagents and chemicals are of analytical grade and are used without further purification.

A mouse fibroblast cell line L929 was provided by the Center for Type Culture Collection, Chinese Academy of Sciences (Shanghai, China). Culture dishes were purchased from Corning Inc. (New York, USA). A Dulbecco's modified Eagle medium (DMEM, Gibco) is supplemented with 10% fetal bovine serum (FBS, Gibco), 100 IU/ml of penicillin and 100 mg/ml of streptomycin sulfate for culture. All cells are cultured in a 37° C., 5% $CO_2$, fully humidified incubator.

Male Sprague-Dawley rats (200±20 g) provided by the Laboratory Animal Center of Wenzhou Medical University (Wenzhou, China) are cultured under the conditions of 25° C. and 55% humidity. All animal experiments are performed in accordance with guidelines assessed and approved by the Ethics Committee.

Preparation Step of Intestinal Anastomosis Stent Taking PTMC as a Base Material Ring-Opening Polymerization of PTMC-b-PEG-b-PTMC A PTMC copolymer is synthesized via ring-opening polymerization. Briefly, a metered amount of PEG monomer is transferred to a completely dry glass reactor with a magnetic stirring rod. $Sn(Oct)_2$ is dissolved in an anhydrous toluene solution under an $N_2$ atmosphere and 100 ppm of the solution is added to the reaction vessel with a pipette. The copolymerization is carried out at 130±2° C. for 24 h to ensure that the whole process is free of water and oxygen. After 24 h, the product is dissolved in chloroform. After complete dissolution, the polymer solution is purified with an excess of n-hexane for 3 times. The purified copolymer is dried in a vacuum drying oven at 40° C. for 48 h and then stored in a drying cabinet.

Preparing Anastomosis Stent by Electrospinning

The dried sample is dissolved in a mixed solution of $CHCl_3$/DMF (9/1, V/V) to prepare a solution with a concentration of 5.5%, and placed on a shaker at 37° C. for 36 h to sufficiently dissolve the sample, so as to obtain a uniform co-dissolved spinning stock solution. The stock solution is loaded into a 2.5 ml syringe comprising a metal needle with an internal diameter of 0.5 mm. Specific spinning conditions are detailed in Table 1[30]. The sample thickness after spinning is 0.2±0.01 mm. The resulting fibers are further dried in the vacuum drying oven at room temperature for 24 h to remove residual organic solvents and moisture. The spun samples are used for mechanical property testing as well as in vitro degradation testing.

TABLE 1

Electrospinning conditions

| Needle pushing speed | Distance from needle to receiver | Rotation speed of roller | Voltage | Temperature | Humidity |
|---|---|---|---|---|---|
| 1.0 mL/h | 20 cm | 400 RMP | 15 V | 35° C. | 25% |

Characterization

Physicochemical Characterization

An FTIR-ATR spectrum of the polymer PTMC is measured with a Nicolet Magna-560 spectrometer equipped with an ATR accessory. A $^1$H-NMR spectrum of the copolymer PTMC is measured with a Bruker spectrometer. All $^1$H-NMRs take tetramethylsilane (TMS) as an internal reference and deuterated chloroform ($CDCl_3$) as a solvent, and record chemical shifts (D) of samples in ppm as unit. A Hitachi cold field emission electron microscope SU8010 field emission scanning electron microscope is used to photograph a micro-morphology of each sample after electrospinning and a micro-morphology after degradation in the implanted animals. The thermal properties of the polymer PTMC are recorded with DSC analysis using DSC8000 (PerkinElmer, USA) at a ramp rate of 10° C./min. The intrinsic viscosity of PTMC is determined using an ubbelohde viscometer in a thermostatic water bath at 25° C. The test result is an average stress-strain of three experiments on an electronic universal material testing machine (Instron5944). The sample after electrospinning is treated as a sheet material with the size of 45.0 mm×25.0 mm, and the size of SD rat cecum is 45.0 mm×25.0 mm×0.3 mm. The sample is rinsed with normal saline, and the excess water on the surface is wiped off.

In Vitro Enzymatic Degradation

A PTMC film with the size of 10.0×10.0 mm is taken, placed in 1 mL of lipase solution with an air bath at 37° C., and shaken for 8 h each day, with an amplitude of 65 times/min. The enzyme solution is changed every 3 days to maintain enzyme activity, samples are taken after 1, 5, 10, 15, 20, 30, 40 and 50 days respectively, and 3 parallel strips are randomly taken. After the sample is sufficiently washed with distilled water, filter paper suctions the surface moisture to dryness in vacuum at 37° C. for 12 h to constant mass. The mass of the dried sample and the pH of a medium containing degradation products are recorded.

An in vivo bio-degradation behavior is obtained by recording the mass and size of the anastomosis stent before and after implantation. After taking out the anastomosis stent, distilled water is used to clean it, and the filter paper suctions the surface moisture to dryness. The weight loss rate is calculated by the following formula:

$$\text{Weight loss (\%)} = (W_0 - Wt)/W_0 \times 100\%$$

where $W_0$ and $Wt$ represent the dry weights of the sample before and after degradation, respectively.

Biological Characterization

Hemolysis Study of Copolymer

The sample material is previously rinsed with distilled water, wiped clean to indicate excess moisture, and fresh human whole blood is used. Experimental group: 15 mg of electrospun sample is taken and placed in an EP tube, added with 1 mL of normal saline and 0.1 mL of whole blood; negative control group: 1 mL of normal saline and 0.1 mL of whole blood are added into the EP tube; positive control group: the EP tube is filled with 1 mL of ultrapure water and 0.1 mL of whole blood. All the samples are incubated at 37° C. for 2 h for hemolysis test.

All test samples are centrifuged at 3000 rpm for 10 min, and the centrifugation is repeated if the supernatant is not clear. After photographing, the supernatant is aspirated and transferred into a well plate, three parallel samples are prepared of the supernatant of each sample, 200 µL of each sample is transferred, the absorbance (OD) is measured at 540 nm of wavelength with a 721 spectrophotometer and the results are recorded.

Data processing: the mean values of OD of three samples in a sample group and a control group are taken, respectively. The hemolysis rate of each sample is calculated according to the formula.

$$H(\%) = \frac{ODt - ODnc}{ODpc - ODnc} \times 100\%$$

where H % is the hemolysis rate, $OD_t$ is the absorbance of the sample, $OD_{nc}$ is the absorbance of a negative control sample and $OD_{pc}$ is the absorbance of a positive control sample. According to GB/T1423.2-1993 standard, through the determination of erythrocyte lysis and hemoglobin free degree caused by a material in contact with red blood cells in vitro, the in vitro hemolysis of the material is evaluated, and the hemolysis reaction of more than 5% is positive.

Cytotoxicity Study

A CCK-8 method is used for toxicological study of experimental samples, and the experimental procedures are as follows:

Preparation of cell culture solution: 500 mL of RPMI1640 medium+50 mL of fetal bovine serum+5 mL of penicillin/streptomycin double antibody.

Preparation of extract of the experimental group: the samples are sterilized with 75% alcohol prior to ultra-clean bench ultraviolet irradiation for 30 min on both sides. The electrospun samples are cut into square films with a side length of 1.82 cm, added with 2 mL of complete medium, and performed with a bathing at 37° C. for 24 h to obtain an extract of the electrospun sample.

Cell preparation: cell culture liquid is used to culture L929 cells (adherent cells) in vitro, proliferate for more than 3 generations, and then grow all over the culture flask. Rinsing is performed for three times with PBS (do not face cells to prevent the cells from being washed out). It is then digested with 50 μL of 0.25% trypsin for 30 s (37° C.) to become a cell suspension. 3-5 mL of complete medium is immediately added and transferred to a centrifuge tube and centrifuged at 1000 rpm for 5 min, upper waste liquid is discarded, 5 mL of PBS is added to the centrifuge tube, and the pipette is purged to evenly disperse the cells. 1 μL of the mixed solution is added to a counting plate for cell counting, and a cell concentration is adjusted to $5 \times 10^4$ cells/mL.

Co-culture: diluted L929 cells are seeded in a 96-well plate at 100 μL per well, and 5000-8000 cells are required per well; after 24 h of culture at 37° C. and 5% $CO_2$, the cells are completely adherent and the culture solution is discarded; 100 μL of the extract from the experimental group and 100 μL of the positive solution (the positive control group is 10% DMSO (200 μL)) are added into wells, with 6 replicate wells in each group and incubated in a 37° C. incubator for 24 h.

CCK-8 assay: a 96-well plate is taken out at preset time points (24 h and 48 h), the stock solution is suctioned out and added around the sample wells, 10 μL of CCK-8 reagent and 100 μL of complete medium are respectively added into each well (firstly the two solutions are mixed), incubated in the incubator at 37° C. for 2 h, and then a multi-functional microplate reader (absorbance of 450 nm) was used to detect an absorbance (OD) value.

Calculation of relative growth rate of cells: a mean value of OD values of 6 wells are taken for each group, and a relative growth rate (RGR) of cells in each group is calculated according to the following formula:

$$\text{Cell Viability (\%)} = \frac{As - Ab}{Ac - Ab} \times 100\%$$

wherein $A_s$ is an absorbance of an experimental well (with a polymer extract, a cell culture medium, and CCK-8); $A_c$ is an absorbance of a control well (without a polymer extract, with a cell culture medium, and with CCK-8); and $A_b$ is an absorbance of an experimental well (without a polymer extract, without a cell culture medium, and with CCK-8).

Antibacterial Study

50 μL of bacterial stock solution of frozen *Escherichia coli* and *Staphylococcus aureus* are respectively added into a centrifuge tube filled with 5 mL of bacterial culture solution, and incubated in a bacteria incubator for 24 h before use. The material is cut into a circular sheet material with a diameter of 1.0 cm, the excess moisture on the surface is wiped out with 75% alcohol and then cleaned, and ultraviolet disinfection is performed for 30 min. 100 μL of diluted bacteria is respectively taken and evenly coated on a culture medium, the circular sheet material is placed on the culture medium coated with bacteria and incubated in the bacteria incubator at 37° C. for 24 h.

In Vivo Bio-Compatibility Study

Rat In Vivo Assay

The healing of intestinal anastomosis is mainly achieved through inflammatory reactions, cell proliferation, intestinal wall structure reorganization, and so on to achieve mechanical, histological and functional repair for ultimate healing. Functional repair is a rather lengthy process involving digestive absorption, endo- and extra-secretion, nerve repair and transitional complex movement, so mechanical and histological indicators must be achieved before we consider the anastomotic site to complete healing. In combination with the operation of surgery, the following indicators shall be achieved in the animal experiment stage: bursting pressure experiment (an indicator of mechanical healing); abdominal adhesion score (response to local inflammatory conditions near the anastomosis); HE staining, Masson staining and immunohistochemical staining of anastomotic tissues (to evaluate the degree of inflammatory cell infiltration and collagen deposition).

Prior to experiments, the PTMC sample is soaked with 75% alcohol for 10 min, and performed with ultraviolet sterilization for 30 min. 180 general grade Sprague-Dawley male rats weighing 200±10 g are anesthetized with 10% chloral hydrate by intraperitoneal injection according to body weights. The experiments are set in three groups, i.e., a PTMC group as an A group, a TCS/PTMC group as a B group and a blank control group as a C group. Four time points are set up in each group, i.e. 7 days, 14 days, 21 days and 28 days respectively. Parallel group is set up with 5 rats. The rat abdomen is shaved, the abdomen is opened, and the rat cecum is exposed. An incision is made at the middle and upper part of the cecum, with the size of 10±1 mm. The contents in the cecum are cleaned. The A group and the B group are placed in the experimental sample and then sutured. The C group is sutured directly. Four-needle simple interrupted full-thickness suture is used for the suture of the anastomotic site. Taking the cross section of the cecum as an object, full-thickness interrupted suture is performed at 3, 6, 9 and 12 positions corresponding to clock positions, with a needle distance of about 0.4 cm and a spacing of about 0.5 cm. The rats in both groups are given food and water ad libitum immediately after anesthesia.

After surgery, each rat is kept in one cage independently, and the food intake, defecation and behaviors are closely observed. The both groups are compared in terms of the time required by the anastomosis method, postoperative general conditions and death. After reaching the corresponding time points, rats in each group are anesthetized and performed with laparotomy, and abdominal adhesion conditions, the presence or absence of abdominal infection and the presence or absence of anastomotic fistula are observed and recorded.

Abdominal Adhesion Score (Adhesion score)

The postoperative abdominal adhesions of SD rats are graded[31] and quantified to obtain a quantified result[32]. Scoring criteria are (0-3 points):

0 Point: no adhesion;

1 Point: mild adhesion, tissue covering only vicinity of the anastomotic stoma which is easy to separate;

2 Points: moderate adhesion, adhesion occurring between the anastomosis site and intraperitoneal tissue, which is difficult but still possible to separate; and 3 Points: severe adhesion, the anastomotic stoma being surrounded by abdominal tissue or other organ tissue adhesion.

Anastomotic Bursting Pressure

The bursting pressure of anastomotic tissue is an important mechanical indicator to detect the healing strength of anastomotic stoma, which reflects the amount of pressure the intestinal tract can bear and is commonly used to detect the healing strength of the anastomotic stoma.

On postoperative day 7, bursting pressure test is performed on an intestinal segment of the anastomotic stoma using in vitro manometry. The anastomotic stoma and about 5 cm of intestinal tube around it are cut off, and the intestinal content is flushed out of the intestinal tract with normal saline. The abdominal adhesions are appropriately separated, the intestinal segment at each anastomotic site is exposed, one end of the intestinal tract is connected to a pressure gauge (YB-150A precision pressure gauge), two wires are used for bundling and fixing, and further two wires are used to ligate and close the intestinal cavity across the other end of the anastomotic stoma, so that the intestinal tube and the pressure gauge are at the same level. A peristaltic pump is used to uniformly inject methylene blue diluent (0.16 mg/mL) into the intestinal tract at a speed of 10 mL/min, attention is paid to observe the anastomotic stoma, and a reading on the pressure gauge is recorded when there is blue liquid overflow (or sudden pressure drop) at the anastomotic stoma, which is the bursting pressure of the anastomotic stoma.

H&E Staining

H&E staining is also known as Hematoxylin-Eosin staining. The basic principle is as follows: a basic dye Hematoxylin and an acidic dye Eosin are used to interact with the nucleus and cytoplasm respectively, so that a fine structure of a cell changes for its refractive index through colors, a cell image can be clearly presented under a light microscope, and good nucleoplasmic contrast staining can be provided.

A test principle is as follows: Hematoxylin is a blue-violet basic dye that can color the nucleus, and a structure colored by Hematoxylin is itself acidic and has basophili. Eosin is a pink acid dye that can stain the cytoplasm red, and a structure colored by Eosin is itself alkaline and acidophilic. Structures that are not easily colored by Hematoxylin and Eosin are neutrophilic.

Results: the nucleus is blue-purple, the cytoplasm, muscle fibers, collagen fibers, and red blood cells are red to varying degrees, and calcium salts and bacteria are blue or blue-violet.

Rats are sacrificed at designated time points, tissues wrapped by the spun stent and intestines are removed, immobilized with a 4% formaldehyde solution, dehydrated with an ethanol solution, embedded with paraffin, sectioned (4 μm), and subjected to H&E staining. The stained sections are observed by a light microscope. The specific process of section preparation is as follows:

(1) a material is taken, then immobilized, embedded with conventional paraffin, and sections by 4 μm;

(2) the sections are routinely dewaxed with xylene and washed with ethanol at all levels: xylene (I) 5 min→xylene (II) 5 min→100% ethanol 2 min→95% ethanol 1 min→80% ethanol 1 min→75% ethanol 1 min→washed with distilled water for 2 min;

(3) the sections are stained with Hematoxylin for 5 min, and rinsed with tap water;

(4) the sections are differentiated with ethanol hydrochloride for 30 s;

(5) the sections are soaked in tap water for 15 min or in warm water (about 50° C.) for 5 min; and (6) the sections are placed in Eosin liquid for 2 min.

Masson Staining

Masson staining is mainly used for the differential staining of collagen fibers and myofibers, and is used to observe the proliferation and distribution of fibrous connective tissues in diseased tissues. Staining results are black nuclei, red muscle fibers, and blue collagen fibers.

Steps:

the tissues are fixed in 10% neutral formalin solution, washed in running water and routinely dehydrated and embedded.

(1) the sections are routinely dewaxed to water;

(2) an appropriate amount of Weigert Hematoxylum A liquid and an equal amount of Weigert Hematoxylin B liquid are mixed to obtain a mixed solution, that is, a Weigert Hematoxylin staining solution; the sections are stained with the prepared Weigert Hematoxylin staining solution for 5 min-10 min;

(3) the sections are differentiated with an acidic ethanol differentiation solution for 5-15 s, and washed with water;

(4) the sections return to blue for 3-5 min in a Masson bluing solution, and washed with water;

(5) the sections are washed with distilled water for 1 min;

(6) the sections are stained with a ponceau acid fuchsin dye solution for 5-10 min;

(7) a weak acid working solution is prepared according to a ratio of distilled water:weak acid solution=2:1, and the sections are washed with the weak acid working solution for 1 min;

(8) the sections are washed with a phosphomolybdic acid solution for 1-2 min;

(9) the sections are washed with the prepared weak acid working solution for 1 min;

(10) the sections are dehydrated rapidly with 95% ethyl alcohol;

(11) the sections are dehydrated with absolute ethyl alcohol for three times, 5-10 s each time; and

(12) the sections are xylene is transparentized for three times, 1-2 min each time.

Immunohistochemical Staining

The paraffin sections are deparaffinized to water and then the tissue sections are placed in an autoclave containing citrate antigen retrieval buffer (PH of 6.0) for antigen retrieval. A 3% hydrogen peroxide solution (hydrogen peroxide: purified water-1:9) is used to block endogenous peroxidase, added with plus 3% BSA for blocking, and then incubated with a primary antibody overnight at 4° C. A secondary antibody of the corresponding species of the primary antibody is added and incubated at room temperature for 50 min, and the nuclei are stained with hematoxylin. After each incubation, cells are washed twice with PBS. The stained cells are photographed with a fluorescence microscope (NIKON ECLIPSE TI-SR).

Results and Discussion

Synthesis of PTMC and Characterization Results Thereof

Figure 2:
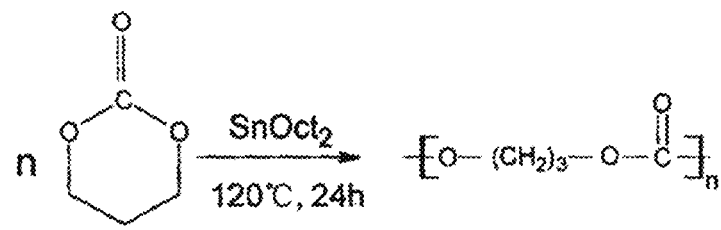
FIG. 2 is a schematic diagram of a PTMC synthesis process of the present invention.

Under the catalysis of $Sn(Oct)_2$, a PTMC copolymer is synthesized by ring-opening polymerization (FIG. 2). The polymerization reaction is as shown in Table 2.

The degradation rates and mechanical properties of copolymers with different molecular weights are very different.

PTMCs with high molecular weights have better degradation rate and shape retention, and different shapes have a significant impact on the degradation rates of the copolymers[35]. Implantation in the intestinal tract requires the products to have a suitable degradation rate and excellent mechanical properties. Therefore, this experiment focuses on the impact of the reaction time on the molecular weights of PTMCs. The reaction time is controlled to obtain PTMCs with different molecular weights. The results of the molecular weights of PTMCs and glass transition temperatures are shown in Table 1. The data show that as the molecular weight increases, the glass transition temperature of PTMC decreases, this is because Tg increases as the crystallinity increases with low molecular weight.

Figure 3:
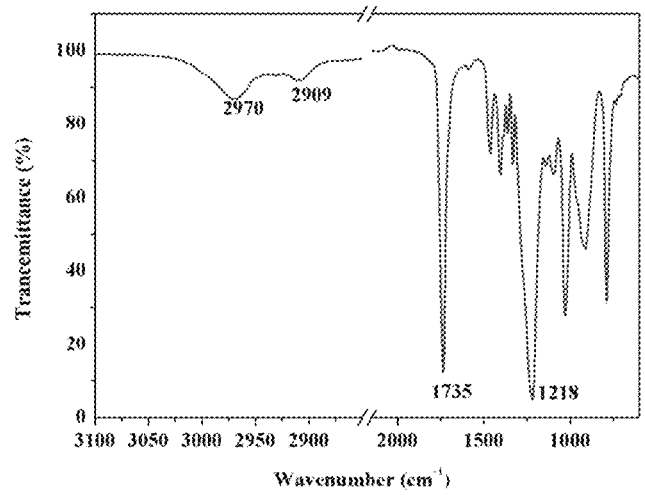
FIG. 3 is an infrared spectrum diagram of PTMC.
Figure 4:
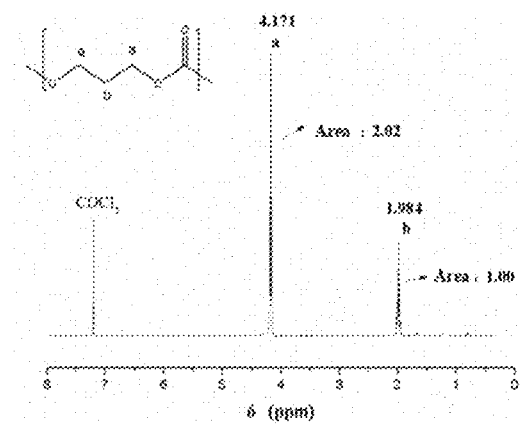
FIG. 4 is a $^1$H-NMR spectrum of a copolymer PTMC.

The infrared spectrum of PTMC is shown in FIG. 3. Stretching vibrations[36] of —$CH_2$-(2970 and 2909 $cm^{-1}$) and C=O (1735 $cm^{-1}$) and —O— (1218 $cm^{-1}$) are observed in PTMC. FIG. 4 is a $^1$H-NMR spectrum of the copolymer PTMC. It clearly shows that the chemical shift S at 4.171 ppm (a) belongs to methylene protons next to the oxygen in a PTMC block, δ at 1.984 ppm (b) belongs to the other methylene protons in the PTMC block, and a ratio of the areas of peaks is consistent with that of the product.

TABLE 2

Synthesis reaction time and physical data of PTMC polymers

| SampleID | Reaction time (h) | Mn ($10^3$) | [η] (dL/g) | Tg (° C.) |
|---|---|---|---|---|
| $PTMC_1$ | 12 | 9.34 | 0.653 | −13.22 |
| $PTMC_2$ | 18 | 30.12 | 0.998 | −14.16 |
| $PTMC_3$ | 24 | 97.09 | 1.339 | −16.36 |
| $PTMC_4$ | 30 | 157.47 | 1.702 | −18.45 |
| $PTMC_5$ | 36 | 200.12 | 2.200 | −19.06 |
| $PTMC_6$ | 42 | 231.87 | 2.292 | −19.00 | a. Determined by [η] = $KM^\alpha$, K = 1.986 × $10^{-4}$, α = 0.789[37]

Evaluation of Mechanical Properties of Electrospun Samples

Figure 5:
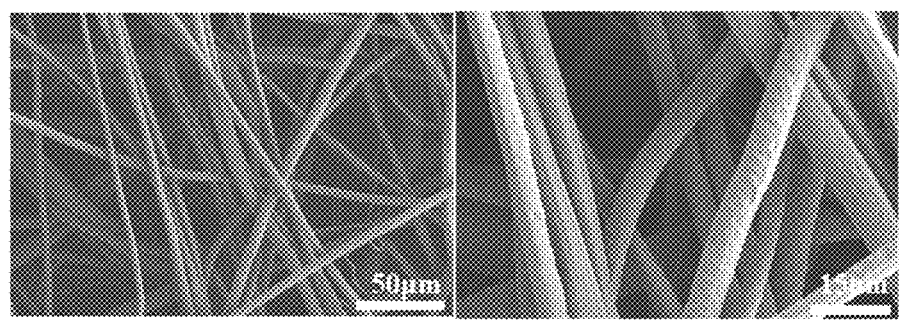
FIG. 5 is an SEM image of an electrospun sample.

The electrospun fibers are evenly distributed and have diameters between 5 μm and 10 μm (FIG. 5).

The mechanical properties of an anastomosis stent prepared by PTMC electrospinning are listed in Table 4. The mechanical property of the stent material under physiological conditions is an important indicator of an implant material. In order to observe the mechanical property of the material under physiological conditions, the sample is soaked in a PBS solution for 24 h before the test, and it is found that the difference in mechanical property of the stent is not large, the tensile strength and the elastic modulus increase to some extent, which is caused by the water absorption of a loose and porous structure of the stent. PTMC with high molecular weight has good mechanical properties and shape retention, while $PTMC_1$ and $PTMC_2$ cannot achieve a good supporting role due to excessively low molecular weights. After the reaction time exceeds 30 h, the mechanical properties of PTMCs do not differ greatly with the increase of reaction time. PTMC as an anastomosis stent has stable mechanical properties in both wet and dry states, which ensures its reliability in practical applications.

TABLE 4

Mechanical properties of PTMC polymers

| Sample ID | $E^a$ (MPa) | $E^b$ (MPa) | $T^c$ (MPa) | $T^d$ (MPa) | $EB^e$ (%) | $EB^f$ (%) |
|---|---|---|---|---|---|---|
| $PTMC_1$ | 9.11 | 9.02 | 3.86 | 3.29 | 40.17 | 41.22 |
| $PTMC_2$ | 11.27 | 11.09 | 5.81 | 5.26 | 60.56 | 65.95 |
| $PTMC_3$ | 18.03 | 16.12 | 15.38 | 13.02 | 153.56 | 165.91 |
| $PTMC_4$ | 20.11 | 19.39 | 16.08 | 14.29 | 170.36 | 180.50 |
| $PTMC_5$ | 20.31 | 19.92 | 16.47 | 15.34 | 180.10 | 184.07 |
| $PTMC_6$ | 21.10 | 20.02 | 17.64 | 15.97 | 186.31 | 192.04 |
| Cecum | — | 5.02 | — | 0.74 | — | 31.24 |

$^a$elastic modulus (finished product),
$^b$elastic modulus (pre-wet for 24 h),
$^c$tensile strength (finished product),
$^d$tensile stregth (pre-wet for 24 h),
$^e$elongation at break (finished product), and
$^f$elongation at break (pre-wet for 24 h)

The dried sample is dissolved in a mixed solution of chloroform/DMF (9/1, V/V) to prepare a solution with a concentration of 5.5%, and placed on a shaker at 37° C. for 36 h to sufficiently dissolve the sample, so as to obtain a uniform co-dissolved spinning stock solution. The stock solution is loaded into a 2.5 ml syringe comprising a metal needle with an internal diameter of 0.5 mm. Specific spinning conditions are detailed in Table 1. The sample thickness after spinning is determined by the specific electrospinning time. The resulting fibers are further dried in the vacuum drying oven at room temperature for 24 h to remove residual organic solvents and moisture. The spun samples are used for mechanical property testing as well as in vitro degradation testing.

| Electrospinning conditions | | | | | |
|---|---|---|---|---|---|
| Needle pushing speed | Distance from needle to receiver | Rotation speed of roller | Voltage | Temperature | Humidity |
| 0.5-2.5 mL/h | 20 cm | 200-400 RMP | 15 V | 35° C. | 25% |

| Needle pushing speed/ mL · $h^{-1}$ | Rotation speed of roller/ RMP | Electro-spinning time/ h | Anastomosis bobbin thickness/ mm | Elastic modulus/ MPa | Elongation at break/ % |
|---|---|---|---|---|---|
| 0.5 | 300 | 5 | 0.05 | 2.13 | 145.2 |
| 1.5 | 200 | 5 | 0.10 | 5.93 | 378.8 |
| 2.0 | 350 | 7 | 0.15 | 9.12 | 704.6 |
| 1.0 | 270 | 12 | 0.2 | 14.77 | 933.2 |
| 2.5 | 300 | 10 | 0.25 | 17.22 | 1192.3 |
| 1.8 | 220 | 20 | 0.30 | 19.68 | 1269.7 |

In Vitro Biodegradation Evaluation

PTMC is mainly degraded by in vitro enzymatic hydrolysis and in vivo surface erosion. Feijen et al. believe that enzymes play an interfacial activation role, so the degradation rate in an in vitro enzyme solution is faster than in vivo degradation. The degradation rates of PTMC materials of the same size and different thicknesses differ greatly. As an intestinal stent, we investigate the degradation differences of film materials of different molecular weights and different thicknesses after electrospinning.

Figure 6A:
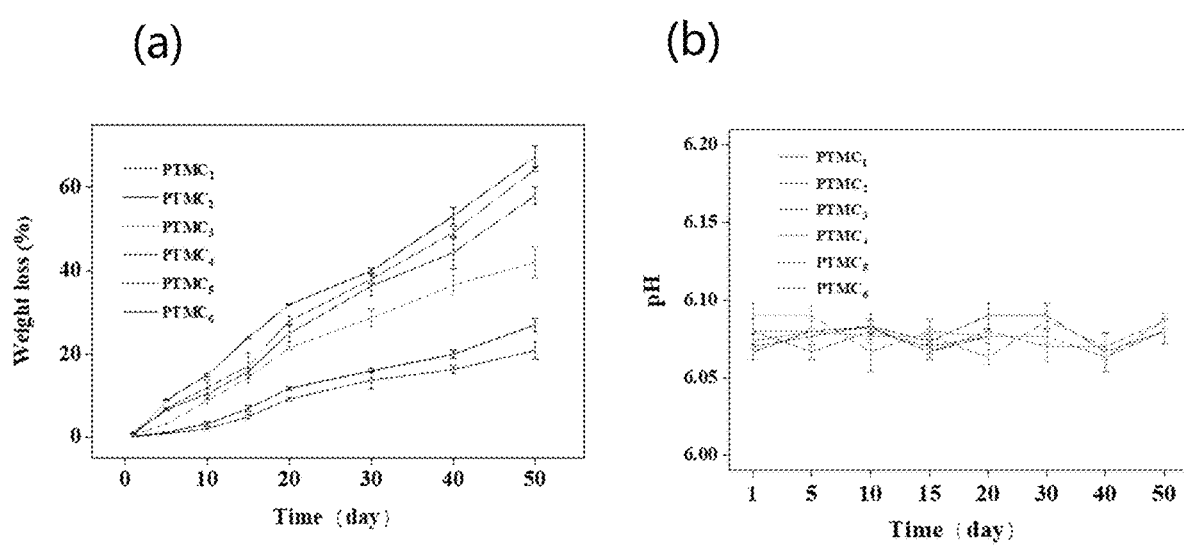
FIGS. 6A and 6B show (A) the degradation time of PTMC films with different molecular weights, (B) the pH curves of lipase solutions after enzymatic degradation of PTMC films with different molecular weights, (C) the degradation time of PTMC films with different thicknesses, (D) SEM of the anastomosis stent after implementation, (E) a physical diagram of the degradation of the anastomosis stent, (F) the weight loss of anastomosis stents removed from rats at corresponding times, and (G) the length loss of anastomosis stents removed from rats at corresponding times.

The object of this animal experiment is male SD rats, and the intestinal healing period of rats is about 14 days. Therefore, the anastomosis stent implanted in the intestinal tract should meet the requirements of mechanical strength for at least two weeks and degradation for about three weeks. The effect of the molecular weight on weight loss rate is studied first (FIG. 6A(a)). $PTMC_{1-7}$ is cut into films of the same size (10.0×10.0×0.4 mm). The results show that degradation is accelerated with the increase of PTMC molecular weight, and the degradation process is acid-free (FIG. 6A(b)). If the molecular weight of PTMC is too low, as shown by $PTMC_1$ and $PTMC_2$, only 20% of weight loss is shown at Day 50, with too slow degradation; and when the molecular weight is more than 150,000, the weight loss of PTMC at Day 50 can reach 60%, which is eligible for implantation in the intestinal tracts of rats. Secondly, we investigate the effects of materials of different thicknesses on weight loss (FIG. 6B(c)). $PTMC_4$ is selected with a length and width of 10.0 mm, and a thickness of 0.10 mm, 0.20 mm, 0.30 mm, 0.40 mm and 0.50 mm, respectively. It can be found that the greater the thickness, the slower the degradation. For $PTMC_4$, when the thickness is 0.2 mm, the degradation rate in the in vitro enzyme solution satisfies our conditions. Based on the comprehensive factors of electrospinning and in vitro enzyme solution degradation and mechanical properties, we believe that the stent with a molecular weight of 150,000-250,000 and a thickness of 0.2 mm is in line with our expectations. In this study, the rat caecum is implanted with a $PTMC_4$ with a thickness of 0.2 mm as an anastomosis stent to observe the subsequent degradation and healing promotion in vivo.

Figure 6B:
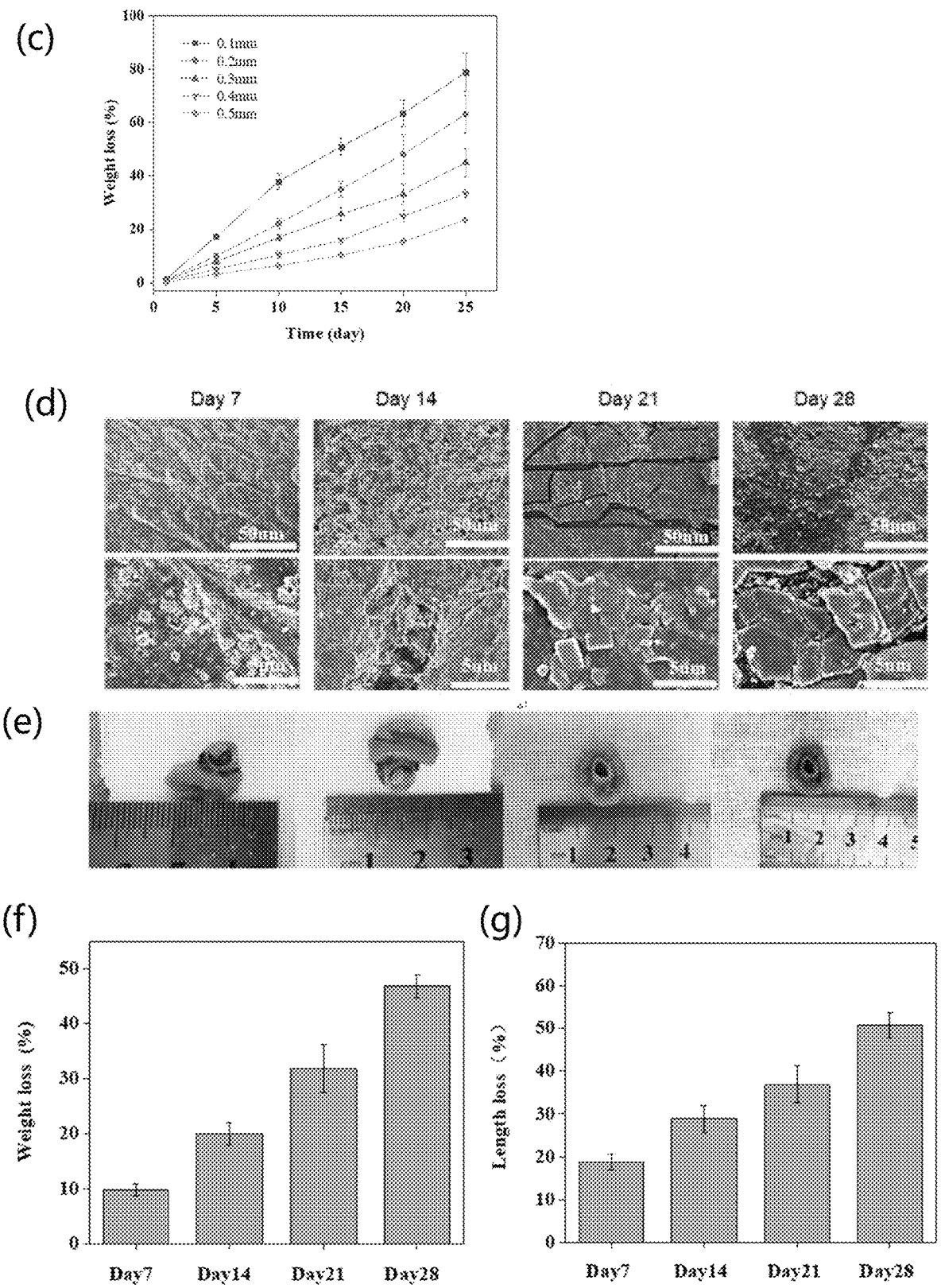

Microscopic morphology is observed after removal of the in vivo anastomosis stent at the corresponding time point (FIG. 6B(c)). Both the weight and the length of the anastomosis stent are reduced to varying degrees (FIGS. 6B (e), (f)), with a weight reduction of more than 40% after 28 days and a length reduction of 50%, reaching a support on mechanical properties for two weeks. After in vivo degradation, the morphology had already started to disintegrate, but the macroscopic integrity remains better (FIG. 6B (d)).

In Vitro Biological Evaluation

Antibacterial

It is well known that the wound healing process may be infected with bacteria, which will delay wound healing. There are numerous microorganisms and bacteria in the intestinal tract, with the number of bacteria reaching the order of $10^{14}$ and more than 1000 species. Compared with other epithelia, the intestinal healing faces a higher density of pathogenic bacteria, which will disturb the normal physiological process of wound healing. Due to the particularity of surgical site, it is difficult to maintain a relatively clean environment for intestinal anastomosis, and the antibacterial and bacterial isolation effect of anastomosis stent plays a very important role.

Figure 7:
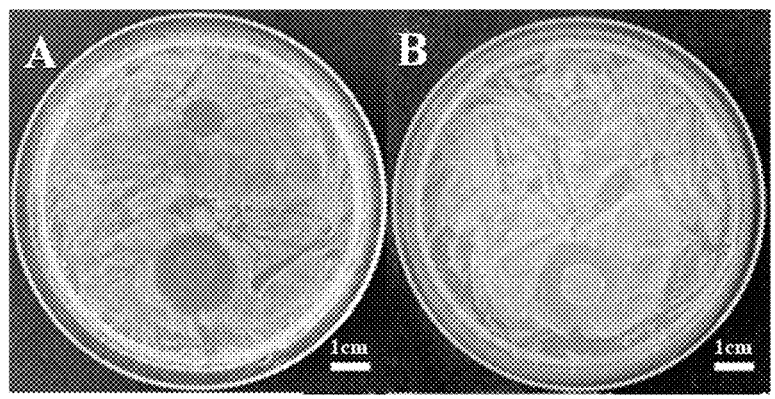
FIG. 7 shows the antibacterial effects of triclosan-free samples (top panel) and triclosan-containing samples (bottom panel), wherein A represents *Staphylococcus aureus*, and B represents *Escherichia coli*.

To address this issue, the antimicrobial agent, triclosan, is added to the sample in a proportion to render the material antimicrobial to ensure relative cleanliness of the wound site. As shown in FIG. 7, the sample without triclosan does not resist bacteria, and the sample with triclosan added has significant zones of inhibition against *Pseudomonas aeruginosa, Escherichia coli* and *Staphylococcus aureus*. Since PTMC degradation, which refers to surface erosion degradation, is a degradation process gradually deep into the interior from the surface, triclosan can be slowly released and always play a bactericidal role.

Hemolysis Rate

Figure 8:
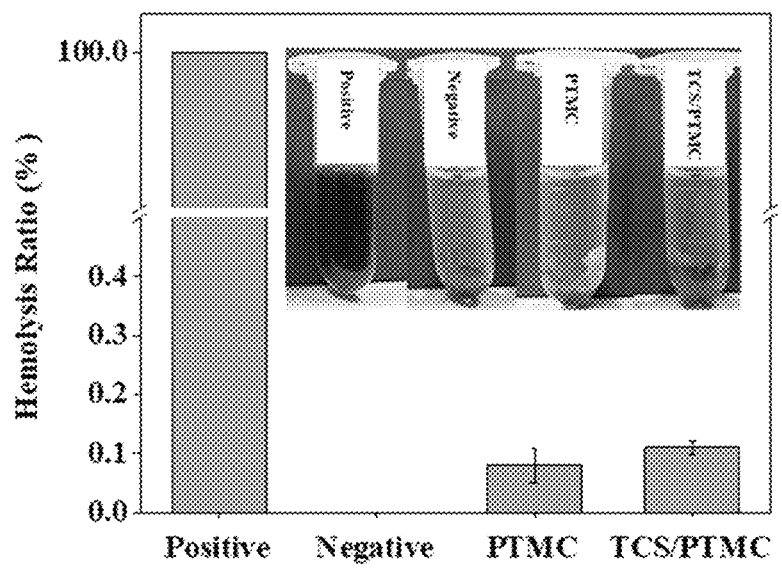
FIG. 8 shows the hemolysis rates of different samples.

Since the anastomosis stent is in direct contact with the site of intestinal anastomotic stoma, if the material causes the rupture of red blood cells, it often causes adenosine diphosphate to be released, accelerating platelet aggregation and thus triggering thrombosis. Hemolysis of anastomosis stents is assessed by direct contact of in vitro materials with blood, and the experimental results are shown in FIG. 8, where the hemolysis rate is less than 0.1%, well below the upper limit of 5% for implantable medical devices.

Cytotoxicity

Figure 9:
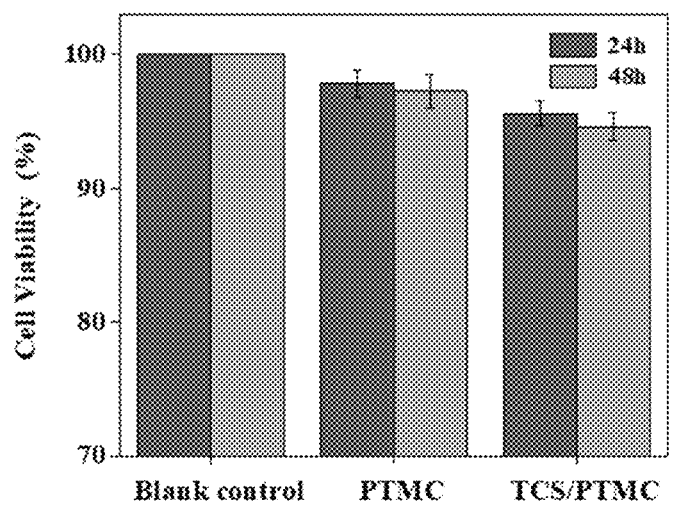
FIG. 9 shows the cytotoxic effects of samples.

L929 cells are used for in vitro experiments of cytotoxicity and cytocompatibility to evaluate the cytocompatibility of pure PTMC and PTMC with triclosan added (FIG. 9). The L929 cells are incubated with the samples for 24 h and 48 h, and the cytotoxicity values of the samples added with triclosan are similar to those of a simple block copolymer, and the cell survival rates are all maintained above 90%, which indicate that the addition of triclosan is effective and feasible, and cannot cause damage to the tissue cells while achieving a bactericidal effect.

Wound Recovery Evaluation

Abdominal Adhesion Score and Anastomotic Bursting Pressure

Figure 10:
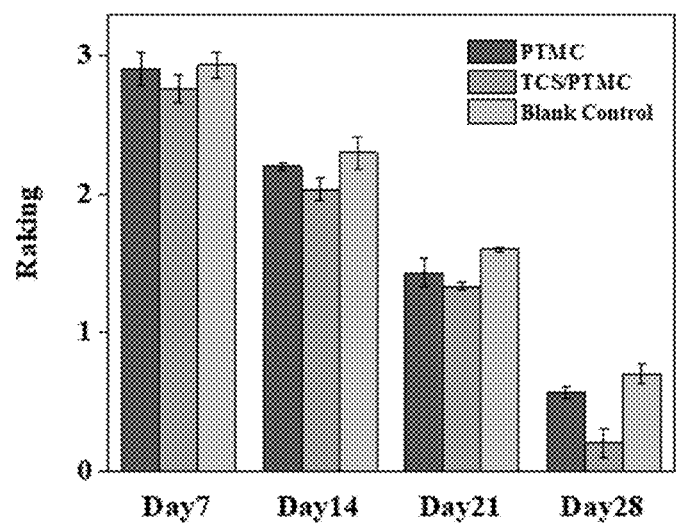
FIG. 10 shows abdominal adhesion scores at various times after intestinal anastomosis.

Laparotomy is respectively performed on the 7th, 14th, 21th and 28th days after surgery, and the abdominal adhesion is scored, for which see FIG. 10 for details. When the abdominal cavity is irritated or infected due to injury, the local area produces a gelatinous fluid of fibrinogen, which is quickly transformed into fibrin clot and covers the mucosal surface of the wound, providing repair protection. Fibrin has a high degree of adhesion that allows the abdominal mucosa to be held close to each other. After the wound heals, there is no trace if the body absorbs the fibrin well, without any trace. In case of incomplete absorption, adhesions may persist and in severe cases may become adhesive ileus, affecting normal physiological activities of the intestinal tract. The anastomosis stent-assisted healing group has significantly less adhesion than the control group, because the anastomosis stent effectively blocks the direct contact between the wound and intestinal contents to reduce the occurrence of infection, so that the anastomotic stoma has better repair and healing speed.

Figure 11:
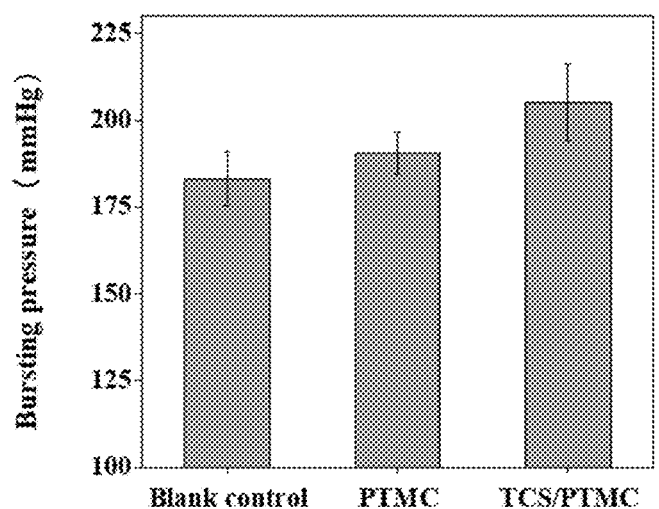
FIG. 11 shows anastomotic bursting pressures of different sample groups 7 days after surgery.

The bursting pressure of anastomotic stoma can effectively reflect the firmness of anastomotic site healing after intestinal anastomosis for a period of time, and this mechanical index can quantitatively reveal the amount of tension the anastomotic stoma can endure. The balance between the deposition of submucosal collagen synthesis and the rate of remodeling is a critical factor in the process of intestinal healing. Insufficient and excessive tissue repair can affect normal bowel function, insufficient repair can result in ulcers and fistulas, and excessive repair can result in fibrosis and stenosis. The remodeling rate of collagen is much higher than the deposition rate in the first 4 days after surgery, and collagen deposition is dominant from the 5th day after surgery, and finally reaches the peak of proliferation phase in the 7th day. Delay or damage to the peak of the proliferative phase can lead to anastomotic dehiscence. Overdeposition and inflammation of collagen can lead to anastomotic strictures. Therefore, on the 7th postoperative day, without affecting the local anastomotic site, the adhesions are separated, then the operative segment cecum is obtained and the bursting pressure experiment of the anastomotic cecum segment is performed (FIG. 11). Bursting pressure of 20 surviving rats in control group is 183 mmHg, which is lower than 190 mmHg (PTMC group) and 205 mmHg (TCS/PTMC group) of the 20 surviving rats in intestinal anastomosis stent group. The anastomosis stent significantly promotes wound healing, and the addition of triclosan isolates bacteria at the wound site, which is beneficial to wound healing. There is statistical difference among the three groups ($P<0.001$).

Histological Analysis

During acute and chronic intestinal inflammation, macrophages and neutrophils induce local tissue damage by secreting reactive oxygen radicals and tissue degrading enzymes. If tissue damage is severe, myofibroblasts can migrate to the defect site. Inflammation is associated with the infiltration of immune cells, such as T cells, macrophages and neutrophils, which also often cause severe damage to a tissue in which inflammation occurs. This persistent inflammation may thus lead to the formation of fibrosis and stenosis.

Figure 12:
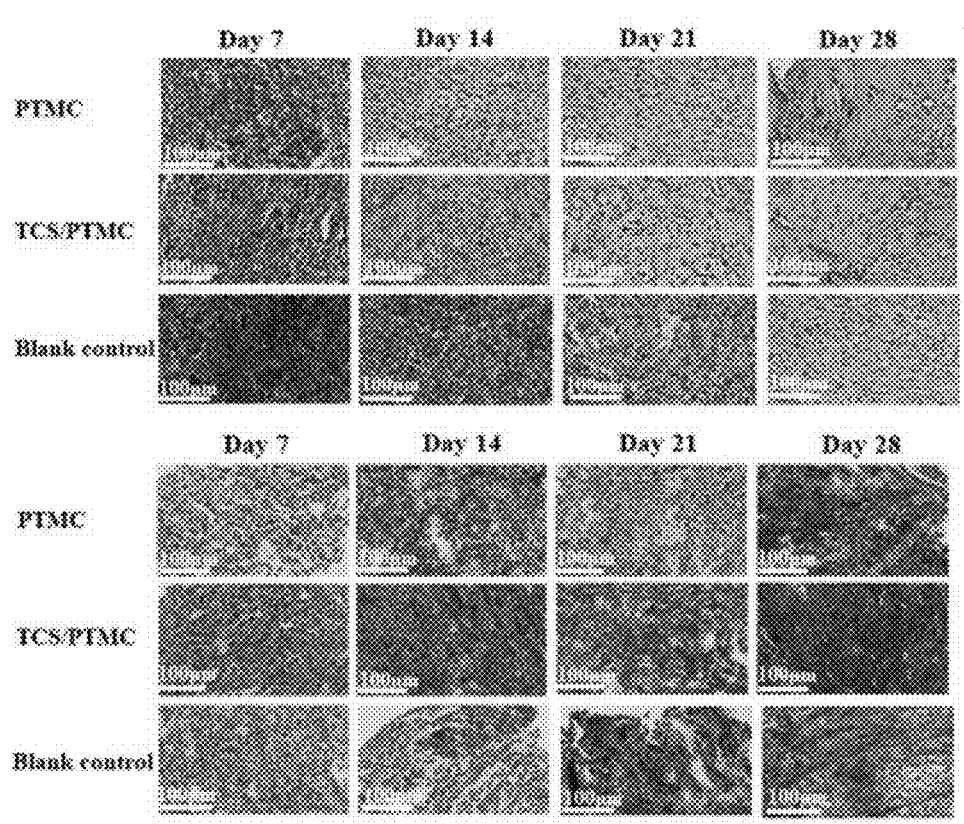
FIG. 12 shows H&E and Masson staining results.

At the corresponding time points after surgery, we perform H&E and Masson staining of an intestinal wall tissue near the anastomosis stoma (FIG. 12). In chronological order, the tissue healing process can be divided into inflammatory phase, proliferation phase and remodeling phase, and the three processes are not strictly defined. In general, the 7th day is a node between the inflammatory phase and the proliferation phase, and the 14th day is a node between the proliferation phase and the remodeling phase. The inflammatory phase is characterized by the accumulation and infiltration of neutrophil-dominated inflammatory cells. In the proliferative phase, the number of fibroblasts is increased, and a large number of disorderly-ranked weak collagen fibers are produced. In the remodeling phase, the acute inflammation is significantly reduced. Instead, the chronic inflammation is marked by the production of multinucleated giant cells, and the collagen fibers are significantly increased. HE staining can show the degree of inflammatory cell infiltration. At the corresponding time points after surgery, the inflammatory cell infiltration in the control group is significantly higher than that in the anastomosis stent-assisted group, and inflammatory cells in the anastomosis stent-assisted group added with triclosan are significantly less than that in an anastomosis stent group without triclosan. Masson staining also verifies the foregoing regulation, in which the stent group reduces the inflammatory reaction due to the exclusion of bacteria, which facilitates the regeneration of fibers, while the addition of triclosan further promotes wound healing.

Immunohistochemical analysis

Wound repair is accomplished by growth factors secreted by cells, such as transforming growth factor-$\beta$ (TGF-$\beta$). TGF-$\beta$ is the most potent and important inducer of $\alpha$-smooth muscle actin ($\alpha$-SMA). TGF-$\beta$ is increased in myofibroblasts at sites of fibrosis in patients with experimental enterocolitis and Crohn's disease. Transforming growth factor can induce the expression of type i collagen, and can effectively stimulate the expression of $\alpha$-SMA. The detection of TGF-$\beta$ level at the wound site can intuitively understand how fast and how well the wound recovers.

Since wound infection is one of the major causes of death in injured patients, a tumor necrosis factor-$\alpha$ (TNF-$\alpha$) is chosen as a monitoring indicator to test the efficacy of anastomosis stents in preventing infection by immunohistochemical analysis.

CONCLUSION

The healing of the intestine after anastomosis is a complex and lengthy physiological process. In fact, intestinal anastomosis consists of three processes: physical healing, histological healing and physiological healing. Physical healing means that after anastomosis of intestinal tract, the intestinal cavity can be closed, intestinal contents can not enter the abdominal cavity, and the intestinal wall can bear certain pressure. Histological healing means that the mucosal layer of the anastomotic stoma is histologically united. The intestinal tract at both ends of the anastomotic stoma regains its original innervation, achieving integrated and orderly intestinal contraction and peristalsis, a process called physiological healing.

The implantation of the anastomosis stent can effectively exclude the adverse factors such as bacteria and viruses, and create a relatively clean environment for the wound, which conclusion is essential for the healing of anastomotic stoma.

Tension at the anastomotic stoma is a major cause of poor healing. This tension may come from the tissue or may result from insufficient blood supply to the constantly tight vessels. The intestinal anastomosis stent prepared in this experiment has tissue flexibility, which can greatly relieve this tension, so that the anastomotic stoma will have a better healing effect.

Notes to technical personnel: although the present invention has been described in accordance with the above specific examples, the invention idea of the present invention is not limited to this invention, and any modification using the idea of the present invention will be included in the protection scope of this patent.

The above is only preferred examples of the present invention, the protection scope of the present invention is not limited to the above examples, all technical solutions belonging to the ideas of the present invention are within the protection scope of the present invention. It should be noted that those of ordinary skill in the art may also make several improvements and modifications without departing from the principles of the present invention, which should be considered as the protection scope of the present invention.

The invention claimed is:

1. A bioabsorbable, flexible elastomeric intestinal anastomosis stent, comprising:
    an inner tubular sleeve made of a plant cellulose material;
    an outer layer made of a polytrimethylene carbonate (PTMC) copolymer material synthesized by a ring-opening polymerization method of a medical polymer material PTMC monomer, the outer layer having a thickness of 0.05-0.3 mm,
    wherein the outer layer on the inner tubular sleeve forms a gapless sleeve-inlaid structure,
    and the outer layer is degradable in vivo within 3 weeks, and the inner tubular sleeve made of a plant cellulose material is decomposable in vivo within 30 minutes.

2. The intestinal anastomosis stent according to claim 1, wherein the PTMC copolymer material is loaded with triclosan (TCS).

3. A method of preparing the intestinal anastomosis stent of claim 1, comprising the following steps:
    (1) ring-opening polymerization of PTMC: transferring a TMC monomer into a reaction vessel, dissolving a catalyst Sn $(Oct)_2$ in an anhydrous toluene solution under a N2 atmosphere, adding 100 ppm of the solution to a reaction vessel with a pipette for copolymerization to ensure that the ring-opening polymerization process is anhydrous and oxygen-free, dissolving the reaction product after 24 h, purifying a polymer solution after complete dissolution, repeating for multiple times, drying the purified copolymer in a vacuum drying oven for 48 h, and then storing the purified copolymer in a drying cabinet; and (2) preparation of the intestinal anastomosis stent by electrospinning: dissolving the dried purified copolymer sample in a $CHCl_3$/DMF mixed solution to form a prepared solution, the prepared solution having a concentration of 5-10.0%, and mixing 0.1-1.0 wt % of an antibacterial agent into the prepared solution to form a mixed solution; after mixing, placing the mixed solution on a shaker at 37° C. for sufficient dissolution of the purified copolymer sample to obtain a uniform co-dissolved spinning stock solution; loading the stock solution into a 2.5 ml syringe, the syringe comprising a metal needle with an inner diameter of 0.5 mm, the sample having a thickness of 0.2±0.01 mm after spinning; and further drying the obtained fiber in the vacuum drying oven at room temperature to remove residual organic solvents and moisture.

4. The method according to claim 3, wherein in the step (1) the product is dissolved at a condition that $CHCl_3$ or DMF or THF is used for dissolution, the product being placed on a shaker, a temperature of the shaker being set at 37° C.

5. The method according to claim 3, wherein the purification in the step (1) is performed at a condition that the purification is performed with n-hexane or ethanol and stirring is continuously performed with a glass rod.

6. The method according to claim 3, wherein $CHCl_3$/DMF in the mixed $CHCl_3$/DMF solution in the step (2) is 1:1.

7. The method according to claim 3, wherein the spinning step in the step (2) is specifically that a plant cellulose tube sleeve of a certain size is sheathed on an electrospinning receiver for spinning, and an intestinal anastomosis stent of a corresponding size is obtained by controlling process parameters, wherein the process parameters include a needle pushing speed V of 1.0-5.0 ml/h, a rotation speed V of a roller of 100-500 RMP, a temperature T of 25-35° C., and a humidity WET of 20-40%.

* * * * *